(12) United States Patent
Faizan et al.

(10) Patent No.: US 11,754,543 B2
(45) Date of Patent: Sep. 12, 2023

(54) HANDHELD DEVICE TO DETECT LEAD COMPOUNDS AND IMPURITIES IN WATER

(71) Applicant: Mirza Faizan, Irving, TX (US)

(72) Inventors: Mirza Faizan, Irving, TX (US); Rafae Qureshi, Frisco, TX (US); Mishaal Qureshi, Frisco, TX (US); Minal Ahmad, Allen, TX (US); Ayaan Nauert, Euless, TX (US); Ibrahim Nauert, Euless, TX (US); Zakaria Shaikh, Allen, TX (US); Fatima Shakeel, Plano, TX (US); Yusra Ali Khan, Plano, TX (US); Mirza Rizwan, Patna (IN)

( * ) Notice: Subject to any disclaimer, the term of this patent is extended or adjusted under 35 U.S.C. 154(b) by 0 days.

(21) Appl. No.: 17/184,930

(22) Filed: Feb. 25, 2021

(65) Prior Publication Data
US 2021/0270793 A1 Sep. 2, 2021

Related U.S. Application Data

(60) Provisional application No. 62/982,182, filed on Feb. 27, 2020.

(51) Int. Cl.
*G01N 33/18* (2006.01)
*G01N 33/24* (2006.01)

(52) U.S. Cl.
CPC ............. *G01N 33/18* (2013.01); *G01N 33/24* (2013.01)

(58) Field of Classification Search
CPC .................. G01N 33/18; G01N 33/24
See application file for complete search history.

(56) References Cited

U.S. PATENT DOCUMENTS

| | | | |
|---|---|---|---|
| 9,991,921 B1* | 6/2018 | Hodge | H04M 1/0202 |
| 2006/0205086 A1* | 9/2006 | Hu | G01N 33/54386 436/514 |
| 2008/0139910 A1* | 6/2008 | Mastrototaro | G16H 20/13 600/365 |
| 2012/0065617 A1* | 3/2012 | Matsiev | A61M 5/142 73/61.61 |
| 2016/0018347 A1* | 1/2016 | Drbal | A61M 1/34 210/647 |
| 2020/0057042 A1* | 2/2020 | Hill | G01N 31/22 |

FOREIGN PATENT DOCUMENTS

WO  WO-2019121609 A1 * 6/2019 ............ A61J 7/0418

* cited by examiner

*Primary Examiner* — Alesa Allgood
*Assistant Examiner* — Sangkyung Lee

(57) ABSTRACT

A simple, sensitive method and device for detecting the LEAD presence in the water. The test involves a sample of water from a subject; followed by determining the presence of LEAD in the water sample by using a LEAD sensitive solution used in the device.

6 Claims, 1 Drawing Sheet

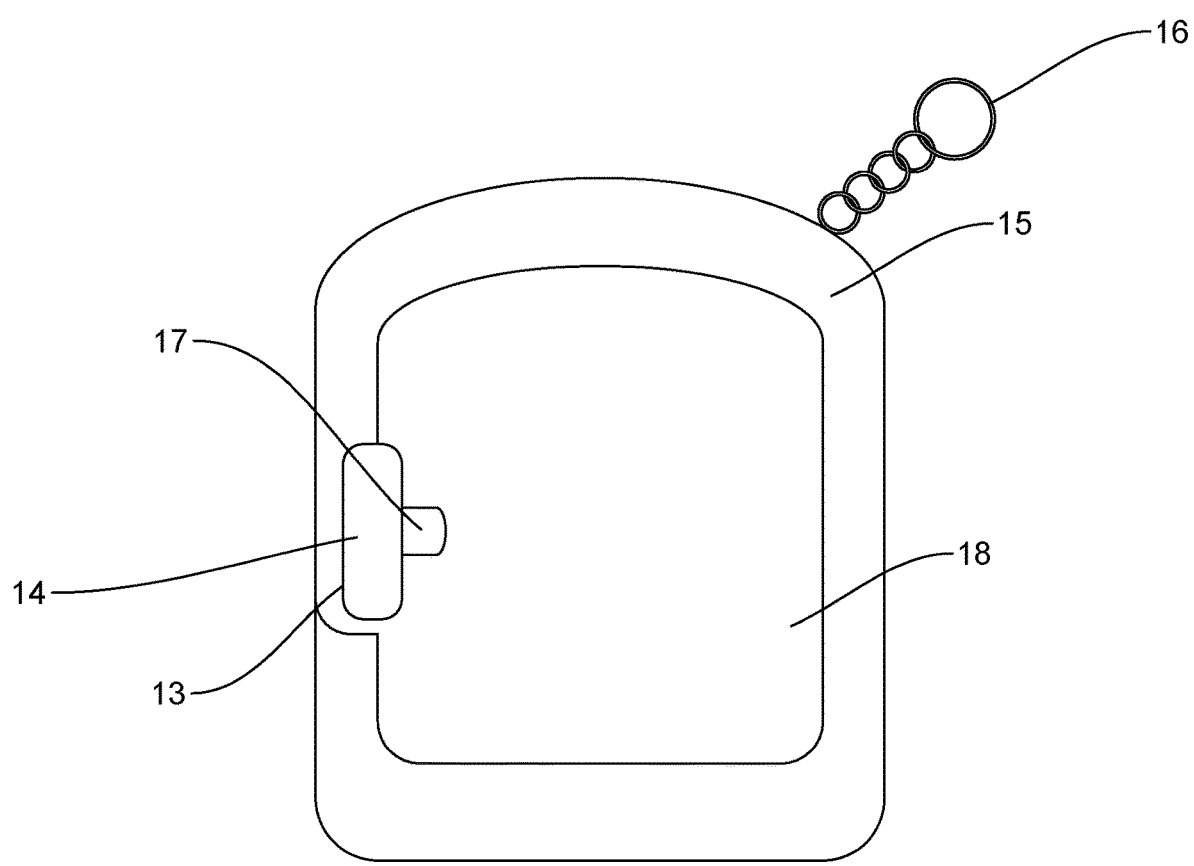

HANDHELD DEVICE TO DETECT LEAD COMPOUNDS AND IMPURITIES IN WATER

TECHNICAL FIELD

The present invention relates generally to water monitoring systems and, more particularly, to a system and device for testing the quality of water and detecting lead compounds in the water using a water impurity detection system or device that simultaneously transmits and records water quality data, with an interactive indicator display to facilitate the display of results for the users.

BACKGROUND OF THE INVENTION

Lead occurs naturally and has been used in many products around the world going back to at least the Roman Empire. As lead has been studied over the years, we keep identifying additional ways that it is toxic. Levels that were once considered safe are now dealt with as a medical emergency. The U.S. Environmental Protection Agency (EPA) continues to research lead to decide if more actions are needed. For public water systems, a law passed in 1986 restricts how much lead can be used in plumbing parts. In 2014, the 1986 law was made even stricter. The EPA has an action level of 15 parts of lead per billion parts of water (ppb) for public water systems. A public water system has to take action to reduce the amount of lead in the water if more than 10 percent of the water samples have lead levels over 15 ppb. This is an action level; there is no safe level of lead in water.

Lead is known to be one of the most dangerous contaminants of drinking water. Some lead compounds that are found in drinking water are very toxic, leading to various illnesses and diseases. This colorless, odorless, and tasteless metal can go undetected in water. Excessive amounts of lead place adults at a higher risk for cancer, stroke, kidney disease, memory problems, and high blood pressure. At even greater risk are children, whose rapidly growing bodies absorb lead more quickly and efficiently. Lead can cause premature birth, reduced birth weight, seizures, hearing loss, behavioral problems, brain damage, learning disabilities, and a lower IQ level in children. The U.S. Environmental Protection Agency (EPA) states that lead is the most serious environmental health hazard for children under the age of 6 years in the United States. Blood tests for lead are often recommended for very young children to determine if lead exposure is occurring.

Because lead is colorless, odorless, and tasteless in water, the only sure way to determine if the water contains lead is to have the water tested. Some labs calculate a corrosivity index from other test results including the pH of the water, but a specific lead test is needed to determine the actual concentration of lead in drinking water. Although regulations are in place to control lead in drinking water, only water testing of each home can determine the actual presence of lead.

To achieve reliable results, such systems or methods often require precision in the realization of a series of time-consuming stages, as well as technical knowledge about the sophisticated operating team of a laboratory. According to these, their use in the detection of lead in water has been essentially limited to clinical facilities that have the necessary resources to make these determinations, including personnel highly trained technicians, and laboratories equipped with equipment appropriate detection.

The conventional systems for water purification have now become passé, creating the requirement for a new detection device and system, as opposed to a filter, that will serve this need to warn the average household user of a potential health hazard not only in the household but quite possibly and much more probably, in the community at large. Existing systems, such as that shown in U.S. Pat. No. 5,865,991, can be used to warn individual consumers but fail to integrate water quality information from a plurality of consumers; such integration not only helps to identify the overall scope of an existing water contamination problem but also enables consumers to be pre-warned of potential problems through notification of surrounding water quality readings.

Previously, a common practice in home water monitoring has been to send an individual sample of water to be tested by way of a water-sampling laboratory, litmus tests, etc. It has become important, however, for public health bacteriologists to have a faster, more accurate way of measuring certain selected characteristics possessed by a single simple sample of common tap water. Also, it is important to note that a single sample is of limited value. The most a single sample can show is the water quality at the time and place of sampling. Therefore, a system is needed whereby repeat samplings may be performed, such as every few weeks.

All of these conventional methods/systems or a device for determining lead in water, and some other method/system presently known in the art have had some flaws in design or mechanism and lacks precision. Most of the existing devices are too expensive and time consuming to bepractical for most users. Some shortfalls of the existing method/system or a device for determining lead in water include a single sample being of limited value. In light of this, there is a need for a method/system or a device for determining lead in water that overcomes these constraints.

In the light of these facts, it is of great advantage to the health and safety of the general public that there is a system or device to accurately tell the level of lead contamination in their drinking water. Furthermore, if a system or device makes its internal calculations and tells the user whether there exists lead contamination in their drinking water, it will save hundreds of lives from being affected by infections and diseases. There is a need for determining lead in drinking water via a system or device that is designed to warn drivers of the presence of lead in their drinking water.

Features and advantages of the invention will be set forth in the description that follows, and in part will be apparent from the description, or may be learned by practice of the invention. The advantages of the invention will be realized and attained by the structure particularly pointed out in the written description and claim hereof as well as the appended drawings.

It is to be understood that both the foregoing general description and the following detailed description are exemplary and explanatory and are intended to provide further explanation of the invention as claimed.

The present invention addresses the issues discussed above.

SUMMARY OF THE INVENTION

In light of the above, the primary object of the present invention is to overcome the disadvantages of the prior arts and provide a system or device for testing the quality of water and detecting lead compounds in the water by using a water impurity detection system or device wherein, the device simultaneously transmits and records water quality data, with an interactive indicator display to facilitate the display of results for the users.

It is an object of the present invention is to disclose a novel apparatus for automatically making intermittent qualitative measurements of the properties of a water sample, to determine if the water meets certain predetermined standards as programmed, and then advancing informational values to the interactive indicator display when the output water quality is below that standard.

It is another related object of the present invention to provide a water analyzing system of the aforementioned type which is particularly useful in determining if drinking water is drawn from a pipe is in a suitable unpolluted condition for an average household consumer.

It is yet another object of the invention to disclose an apparatus that can sense and sequentially record (on a single screen) the level of lead or other component content of a flowing sample of tap water, such that the user can always be assured that he/she has a reliable computer-charted representation of his or her water stream and such water is fit for consumption.

Another object of the invention is a technique for repeatedly testing water samples at a consumer's tap which allows for valid comparison of data collected in different places at various times and identification of trends in water quality.

These and other objects and advantages of the present invention may be achieved through the provision of a system and method of sensing the presence of lead in drinking water and providing a warning alert signal to the user in a more immediate and improved fashion. The device in the present invention comprises of a Chemical Pod, a Hinged Lid, a keychain, and a Chemical Release Button, wherein, the Chemical Pod will be made of polyvinyl alcohol as it is a type of dissolvable plastic and will upto hold 5 mL of Sodium Sulfide as it is an indicator for Lead Acetate, and will be placed inside the pod in the Internal Chemical Pod Chamber.

The method for monitoring the quality of drinking water according to the present invention comprises taking a sample of drinking water, releasing a portion of Sodium Sulfide from the keychain into the water sample, detecting the presence of lead in the sample, and passing that data regarding the presence of the detected material to a common data acquisition network, for recording and displaying the collected data for customers.

Another object of the present invention is that using the simplified device of the present invention can be carried out to perform a qualitative and semiquantitative and easily readable result, which is highly sensitive, specific, and reliable. Normally, it takes as little as a single drop of a sample of test fluid to carry out the test. Also, the device and test of the present invention are particularly advantageous in that it is not only convenient and simple to use, but the device can be stored at room temperature for long periods without decreasing the activity or sensitivity of the test. A further alarm may also be incorporated into the system.

It is another object of the present invention to provide rapid analysis and reliability. There is no required maintenance for such devices, and are not restricted to limited uses. The system exhibits no drift in the response over time and is not affected by interferences such as external factors. Furthermore, the overall system is relatively portable as compared to the prior arts.

Other objects, advantages, and features of this invention will become more apparent from the following description.

The details of one or more implementations are set forth in the accompanying description below. Other aspects, features, and advantages of the subject matter disclosed herein will be apparent from the description and the claims.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

Features, elements, and aspects of the invention that are referenced by the same numerals in different figures represent the same, equivalent, or similar features, elements, or aspects in accordance with one or more embodiments.

The following FIGURE depicts a certain illustrative embodiment of the invention. This depicted embodiment is to be understood as illustrative of the invention and not as limiting in any way.

Referring particularly to the drawing for illustration only and not limitation, there is illustrated:

FIG. 1 shows a front perspective view of the device according to one embodiment of the present invention.

DRAWINGS—REFERENCE NUMERALS

10. Clear Viewing Window
11. Chemical Release Button
12. External Chemical Pod Storage
13. Internal Chemical Pod Chamber
14. Chemical Pod
15. Hinged Lid
16. Keychain
17. Chemical Input Spout
18. Liquid Chamber

DETAILED DESCRIPTION OF DRAWINGS

This invention is susceptible to embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, reference numerals are used to describe the same, similar, or corresponding parts in the several views of the drawings. This detailed description defines the meaning of the terms used herein and specifically describes embodiments for those skilled in the art to practice the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

As used herein the term LEAD detection kit refers to a test kit that involves a user being able to do the test at home, for example, a water test which indicates a positive or negative result by a color change or other means such as a digital output. The home test is designed to be used by someone without any experience and as such the water LEAD detection type tests. The LEAD detection kit is sensitive to the presence of LEAD in water and change color, or otherwise indicate, when above the threshold sensitivity to the LEAD is detected in the particular test. One could easily make even less sensitive tests available with the current technology but until now it has been thought that only more sensitive tests were needed.

Further used herein a test kit is a device with a solution, wherein the solution is sensitive with the LEAD, of the kind used to place water on a particular spot which initiates LEAD in water and color or another indicator test. In newer type testing the LEAD in the water could also be a digital type where an indicator screen displays a message such as safe to drink or not safe to drink instead of a simple color change.

FIG. 1 shows the front perspective view of the device of the present invention wherein a viewing window 10 is located 0.5 inches below a Hinged Lid 15 and a chemical release button 11 as well as a keychain accessory 16. A Chemical Pod 14 is located beside the device. The device further includes an External Chemical Pod Storage 12 as well as the keychain accessory 16 which is attached to the upper right corner of the device, just below the Hinged Lid 15, and the Chemical Release Button 11 which is located in the center of the right side of the device.

According to an embodiment of the present invention, an Internal Chemical Pod Chamber 13 which is located on the right side of the device, 0.5 inches above the bottom end of the device as well as a Chemical Input Spout 17 which is located 0.2 inches above the Internal Chemical Pod Chamber 13 and the Liquid Chamber 18 which is 1×0.5×1 inches. The Chemical Pod 14 will rest on the Internal Chemical Pod Chamber.

In one embodiment, the present invention is a home LEAD testing device, wherein the device comprising a Chemical Pod, and water that to be tested, and at least a chemical that is sensitive to the LEAD present in the water.

It is recognized, however, that departures may be made within the scope of the invention and that obvious modification will occur to a person skilled in the art. concerning the above description then, it is to be realized that the optimum dimensional relationships for the parts of the invention, to include variations in size, materials, shape, form, function, and manner of operation, assembly, and use, are deemed readily apparent and obvious to one skilled in the art, and all equivalent relationships to those illustrated in the drawings and described in the specification are intended to be encompassed by the present invention.

It is therefore submitted that the instant invention has been shown and described in what is considered to be the most practical and preferred embodiments. It is recognized, however, that departures may be made within the scope of the invention and that obvious modification will occur to a person skilled in the art. With respect to the above description then, it is to be realized that the optimum dimensional relationships for the parts of the invention, to include variations in size, materials, shape, form, function, and manner of operation, assembly, and use, are deemed readily apparent and obvious to one skilled in the art, and all equivalent relationships to those illustrated in the drawings and described in the specification are intended to be encompassed by the present invention.

It is noted that various connections are set forth between elements in the description and in the drawings (the contents of which are included in this disclosure by way of reference). It is noted that these connections in general and, unless specified otherwise, may be direct or indirect and that this specification is not intended to be limiting in this respect. In this respect, a coupling between entities may refer to either a direct or an indirect connection.

The disclosed methods and systems, as illustrated in the ongoing description or any of its components, may be embodied in the form of a computer system. Typical examples of a computer system include a general-purpose computer, a programmed microprocessor, a micro-controller, a peripheral integrated circuit element, and other devices, or arrangements of devices that are capable of implementing the steps that constitute the method of the disclosure.

Various implementations of the systems and techniques described here can be realized in digital electronic circuitry, integrated circuitry, specially designed ASICs (application-specific integrated circuits), computer hardware, firmware, software, and/or combinations thereof. These various implementations can include implementation in one or more computer programs that are executable and/or interpretable on a programmable system including at least one programmable processor, which may be special or general-purpose, coupled to receive data and instructions from and to transmit data and instructions to, a storage system, at least one input device, and at least one output device.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

While in the foregoing specification, several embodiments of the invention have been set forth for purposes of making a complete disclosure, it will be apparent to those skilled in the art that numerous changes may be made without departing from the spirit and principles of the invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Although the present invention has been explained in relation to its some embodiments, it is to be understood that many other possible modifications and variations can be made without departing from the Spirit and Scope of the invention as hereinafter claimed.

What is claimed is:

1. A device for detection of LEAD in water, the device comprises:
   an Internal Chemical Pod Chamber located on the right side of the device, 0.5 inches above the bottom end of the device having a sample pad and a solution pad, said sample pad adapted to collect a water sample and deliver the water sample to the solution pad; and wherein said sample pad and said solution pad are in fluid communication;
   a Liquid Chamber measuring 1 inch by 0.5 inch by 1 inch, positioned adjacent to the Internal Chemical Pod Chamber;
   a Chemical Pod placed at an inner portion of the Internal Chemical Pod Chamber, which is located on the right side of the device, 0.5 inches above the bottom end of the device, wherein the Chemical Pod is adapted to store a solution which is sensitive with said LEAD, wherein the Chemical Pod comprises a Chemical Input Spout to deliver the solution to the solution pad;

a push-button attached with the Chemical Input Spout adapted to release the solution at the solution pad from the Chemical Input Spout of the Internal Chemical Pod Chamber, thereby presence of said LEAD in said water is detected above a predetermined threshold, wherein the predetermined threshold is based on a minimum LEAD that is present in the water without affecting a user of the device; and a keychain accessory attached with upper right corner of the device, wherein the keychain accessory is configured to hold the device and make the device portable and wherein the device can be stored at room temperature.

2. The device of claim 1, wherein said opening is centrally located on the upper end of said device.

3. The device of claim 1, wherein when the presence of LEAD in said water is above the predetermined threshold, then a POSITIVE result is obtained.

4. The device of claim 3, wherein an alarm is triggered when the POSITIVE result is obtained.

5. The device of claim 1, wherein said Internal Chemical Pod Chamber is directly connected to a push-button.

6. The device of claim 1, wherein said solution pad comprises a display portion; said display portion adapted to display a minus sign when the presence of said LEAD in the water sample is absent or below said predetermined threshold.

\* \* \* \* \*